US011341637B2

(12) United States Patent
Iwaki (10) Patent No.: US 11,341,637 B2
(45) Date of Patent: May 24, 2022

(54) ENDOSCOPE IMAGE PROCESSING DEVICE AND ENDOSCOPE IMAGE PROCESSING METHOD

(71) Applicant: OLYMPUS CORPORATION, Hachioji (JP)

(72) Inventor: Hidekazu Iwaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 223 days.

(21) Appl. No.: 16/692,301

(22) Filed: Nov. 22, 2019

(65) Prior Publication Data

US 2020/0090333 A1 Mar. 19, 2020

Related U.S. Application Data

(63) Continuation of application No. PCT/JP2017/019665, filed on May 26, 2017.

(51) Int. Cl.
*G06T 7/00* (2017.01)
*G06T 7/70* (2017.01)
(Continued)

(52) U.S. Cl.
CPC ............ *G06T 7/0012* (2013.01); *A61B 1/045* (2013.01); *G06T 7/70* (2017.01); *G06V 10/25* (2022.01);
(Continued)

(58) Field of Classification Search
CPC ............... G06T 7/0012; G06T 7/70; G06T 2207/10068; G06T 2207/30096;
(Continued)

(56) References Cited

U.S. PATENT DOCUMENTS

2003/0220544 A1\* 11/2003 Chang .................... A61B 1/126
600/156
2005/0015048 A1\* 1/2005 Chiu ...................... A61M 25/10
604/101.04
(Continued)

FOREIGN PATENT DOCUMENTS

JP 2007159738 A 6/2007
JP 2010268961 A 12/2010
(Continued)

OTHER PUBLICATIONS

International Search Report (ISR) dated Aug. 22, 2017 (and English translation thereof), issued in International Application No. PCT/JP2017/019665.
(Continued)

*Primary Examiner* — Jerome Grant, II
(74) *Attorney, Agent, or Firm* — Holtz, Holtz & Volek PC (57) ABSTRACT

An endoscope image processing device includes a processor. The processor sequentially receives an observation image obtained by performing image pickup of an object inside a tubular portion of a subject, performs processing for detecting a region of interest with respect to the observation image, performs judgement processing as to whether degradation of visibility of the region of interest included in the observation image is predicted, and performs emphasis processing for emphasizing the position of the region of interest when a judgement result indicating that the degradation of visibility of the region of interest included in the observation image is predicted is acquired by the judgement processing.

20 Claims, 6 Drawing Sheets

(51) Int. Cl.
*A61B 1/045* (2006.01)
*G06V 10/25* (2022.01)

(52) U.S. Cl.
CPC ............... *G06T 2207/10068* (2013.01); *G06T 2207/30096* (2013.01); *G06T 2207/30168* (2013.01); *G06V 2201/032* (2022.01)

(58) Field of Classification Search
CPC .......... G06T 2207/30168; A61B 1/045; A61B 2090/309; A61B 1/00009; G06K 9/3233; G06K 2209/053; G06K 2209/05; G06K 9/4642; G06K 9/2054; G06K 9/6202
USPC ......................................................... 382/128
See application file for complete search history.

(56) References Cited

U.S. PATENT DOCUMENTS

| | | | | |
|---|---|---|---|---|
| 2010/0274086 | A1* | 10/2010 | Diehl | ................. A61B 1/00158 600/118 |
| 2011/0267444 | A1* | 11/2011 | Yamaguchi | ............ H04N 7/183 348/65 |
| 2012/0257167 | A1* | 10/2012 | Gille | ...................... A61B 3/117 351/219 |
| 2014/0248649 | A1* | 9/2014 | Mayer | .................... G02B 21/28 435/29 |
| 2016/0336145 | A1* | 11/2016 | Ominami | .............. H01J 37/222 |
| 2018/0051553 | A1* | 2/2018 | Indo | ........................ E21B 49/10 |
| 2018/0242817 | A1 | 8/2018 | Imaizumi et al. | |

FOREIGN PATENT DOCUMENTS

| | | | | |
|---|---|---|---|---|
| JP | 2011115252 | A | 6/2011 | |
| JP | 2011255006 | A | 12/2011 | |
| JP | 2015096237 | | * 5/2015 | ............. G02B 23/14 |
| WO | 2017073338 | A1 | 5/2017 | |

OTHER PUBLICATIONS

Written Opinion of the International Searching Authority dated Aug. 22, 2017 issued in International Application No. PCT/JP2017/019665.

* cited by examiner

ENDOSCOPE IMAGE PROCESSING DEVICE AND ENDOSCOPE IMAGE PROCESSING METHOD

CROSS REFERENCE TO RELATED APPLICATION

This application is a continuation application of PCT/JP2017/019665 filed on May 26, 2017, the entire contents of which are incorporated herein by this reference.

BACKGROUND OF THE INVENTION

1. Field of the Invention

The present invention relates to an endoscope image processing device and an endoscope image processing method.

2. Description of the Related Art

In endoscope apparatuses, operators have conventionally determined the presence or absence of lesioned parts, etc. by viewing observation images. In order to prevent operators from overlooking lesioned parts when observing observation images, an endoscope apparatus has been proposed which displays an observation image while adding an alert image to a region of interest detected by image processing as disclosed in Japanese Patent Application Laid-Open Publication No. 2011-255006.

SUMMARY OF THE INVENTION

An endoscope image processing device according to an aspect of the present invention includes a processor. The processor sequentially receives an observation image obtained by performing image pickup of an object inside a tubular portion of a subject, performs processing for detecting a region of interest with respect to the observation image, performs judgement processing as to whether degradation of visibility of the region of interest included in the observation image is predicted, and performs emphasis processing for emphasizing the position of the region of interest when a judgement result indicating that degradation of visibility of the region of interest included in the observation image is predicted is obtained by the judgement processing.

An endoscope image processing method according to an aspect of the present invention performs processing for detecting a region of interest with respect to an observation image obtained by performing image pickup of an object inside a tubular portion of a subject, performs judgement processing as to whether degradation of visibility of the region of interest included in the observation image is predicted, and performs emphasis processing for emphasizing the position of the region of interest when a judgement result indicating that degradation of visibility of the region of interest included in the observation image is predicted is obtained by the judgement processing.

DETAILED DESCRIPTION OF THE PREFERRED EMBODIMENT(S)

An embodiment according to the present invention will be described hereunder with reference to the drawings.

Figure 1:
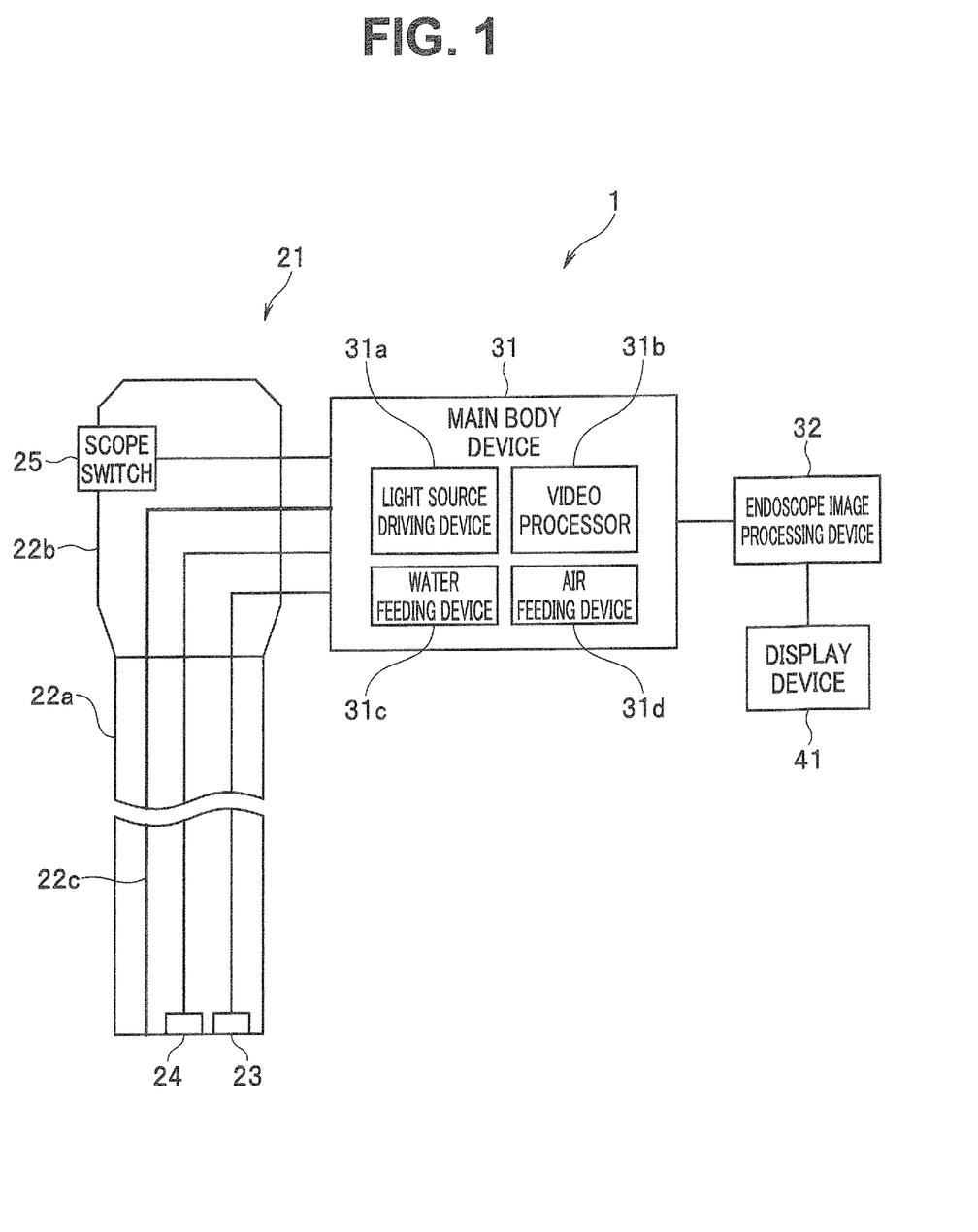
FIG. 1 is a diagram showing a configuration of a main part of an endoscope system including an endoscope image processing device according to an embodiment.

As shown in FIG. 1, an endoscope system 1 is configured to include an endoscope 21, a main body device 31, an endoscope image processing device 32, and a display device 41. FIG. 1 is a diagram showing a configuration of a main part of the endoscope system including the endoscope image processing device according to the embodiment.

The endoscope 21 is configured to be freely detachably connected to the main body device 31. The endoscope 21 is configured to include an elongated insertion portion 22a that is insertable into a luminal organ of a subject person, and an operation unit 22b provided at a proximal end portion of the insertion portion 22a. Furthermore, the endoscope 21 is provided with a channel 22c, one end of which is attachable to and detachable from the main body device 31, and the other end of which is arranged at a distal end portion of the insertion portion 22a.

A light source unit 23 and an image pickup unit 24 are provided at the distal end portion of the insertion portion 22a.

The light source unit 23 is configured to include a light emitting element such as a white LED. The light source unit 23 is configured to generate illumination light by emitting light according to a light source drive signal supplied from the main body device 31, and emit the generated illumination light to an object such as a living tissue.

The image pickup unit 24 is configured to include an image sensor such as a color CCD or a color CMOS. The image pickup unit 24 is configured to perform an operation responding to an image pickup control signal outputted from the main body device 31. Furthermore, the image pickup unit 24 is configured to receive reflected light from the object which is illuminated with the illumination light emitted from the light source unit 23, picks up an image of the received reflected light to generate an image pickup signal, and outputs the generated image pickup signal to the main body device 31.

The operation unit 22b is configured to have a shape that enables a user such as an operator to grip and operate the operation unit 22b. Furthermore, the operation unit 22b is provided with a scope switch 25 having one or more switches for performing an instruction corresponding to a user's operation on the main body device 31.

For example, the scope switch 25 is provided with a water feeding switch (not shown) which is a push button switch capable of issuing an instruction for causing water to be jetted to the front side of the distal end portion of the insertion portion 22a (hereinafter, abbreviated as a water feeding instruction), and an air feeding switch (not shown) which is a push button switch capable of issuing an instruction for causing air to be jetted to the front side of the distal end portion of the insertion portion 22a (hereinafter, abbreviated as an air feeding instruction).

The channel 22c is configured as a conduit having an inner diameter which enables fluid (water and/or air) supplied from the main body device 31 to flow through the channel 22c. Furthermore, the channel 22c is configured by providing the distal end portion of the insertion portion 22a with an opening portion (not shown) through which the fluid supplied from the main body device 31 is jetted.

The main body device 31 is configured to be freely detachably connected to each of the endoscope 21 and the endoscope image processing device 32. The main body device 31 is configured to include a light source driving device 31a, a video processor 31b, a water feeding device 31c, and an air feeding device 31d.

The light source driving device 31a is configured to include, for example, a drive circuit. The light source driving device 31a is configured to generate a light source drive signal for driving the light source unit 23 based on the light source control signal from the video processor 31b, and output the generated light source drive signal to the endoscope 21.

The video processor 31b is configured to generate a light source control signal for controlling the light emission state of the light source unit 23 and output the light source control signal to the light source driving device 31a. Furthermore, the video processor 31b is configured to generate an image pickup control signal for controlling the image pickup operation of the image pickup unit 24 and output the generated image pickup control signal to the endoscope 21. Still furthermore, the video processor 31b is configured to perform predetermined processing on the image pickup signal outputted from the endoscope 21 to generate an observation image G1 of an object, and successively output the generated observation image G1 to the endoscope image processing device 32 frame by frame.

The water feeding device 31c is configured to include, for example, a pump and a tank for water feeding. Furthermore, the water feeding device 31c is configured to perform an operation for supplying water stored in the tank to the channel 22c when detecting a water feeding instruction from the operation unit 22b. In addition, the water feeding device 31c is configured to generate a water feeding instruction detection signal which is a signal indicating the presence or absence of a water feeding instruction from the operation unit 22b and output the generated water feeding instruction detection signal to the endoscope image processing device 32.

The air feeding device 31d is configured to include, for example, a pump and a bomb for air feeding. Furthermore, the air feeding device 31d is configured to perform an operation for feeding air stored in the bomb to the channel 22c when detecting an air feeding instruction from the operation unit 22b. In addition, the air feeding device 31d is configured to generate an air feeding instruction detection signal which is a signal indicating the presence or absence of an air feeding instruction from the operation unit 22b, and output the generated air feeding instruction detection signal to the endoscope image processing device 32.

Figure 2:
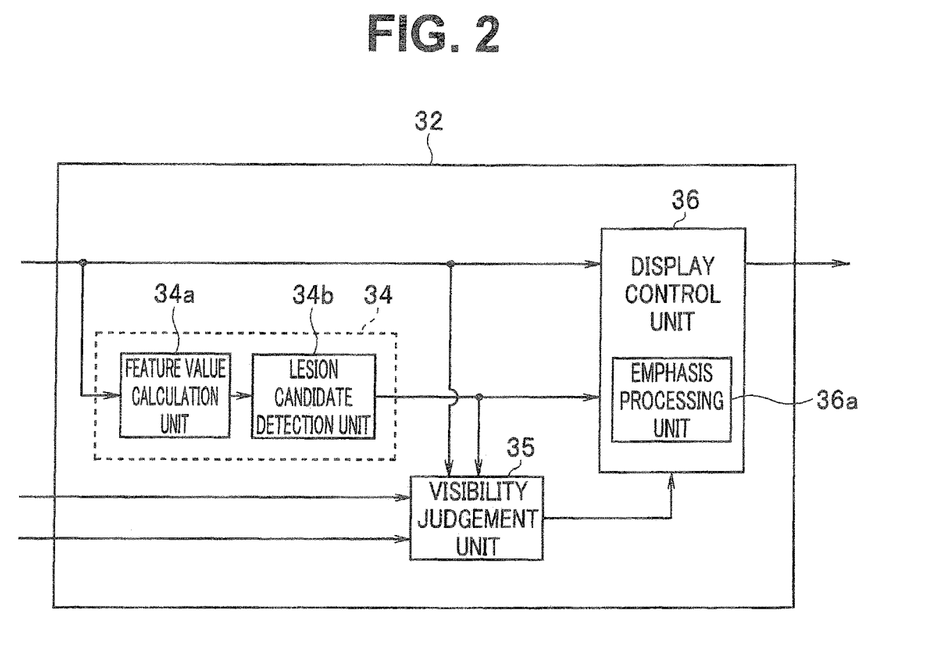
FIG. 2 is a block diagram showing an example of a specific configuration of the endoscope image processing device according to the embodiment.

The endoscope image processing device 32 is configured to be freely detachably connected to each of the main body device 31 and the display device 41. Furthermore, the endoscope image processing device 32 is configured to generate a display image based on the observation image G1 outputted from the main body device 31 (video processor 31b), and perform an operation of causing the display device 41 to display the generated display image. In addition, as shown in FIG. 2, the endoscope image processing device 32 is configured to include a region-of-interest detection unit 34, a visibility judgement unit 35, and a display control unit 36. Note that according to the present embodiment, for example, each unit of the endoscope image processing device 32 may be configured as an individual electronic circuit, or configured as a circuit block in an integrated circuit such as FPGA (field programmable gate array). According to the present embodiment, for example, at least a part of the endoscope image processing device 32 may be configured by CPU. FIG. 2 is a block diagram showing an example of a specific configuration of the endoscope image processing device according to the embodiment.

The region-of-interest detection unit 34 is configured to calculate a predetermined feature value related to the observation image G1 sequentially outputted from the main body device 31, and further detect, based on the calculated predetermined feature value, a lesion candidate region L that is a region of interest included in the observation image G1. In other words, the region-of-interest detection unit 34 is configured to sequentially receive a plurality of observation images G1 obtained by picking up images of an object with the endoscope 21, and perform processing for detecting a lesion candidate region L for each of the plurality of observation images G1. Furthermore, as shown in FIG. 2, the region-of-interest detection unit 34 is configured to include a feature value calculation unit 34a and a lesion candidate detection unit 34b.

The feature value calculation unit 34a is configured to calculate a predetermined feature value related to the observation image G1 sequentially outputted from the main body device 31, and output the calculated predetermined feature value to the lesion candidate detection unit 34b.

Specifically, for example, the observation image G1 is divided into a plurality of small regions each having a predetermined size, and the feature value calculation unit 34a calculates, as a feature value for each small region of the plurality of small regions, an inclination value which is a value indicating the amount of variation in brightness or the amount of variation in density in each pixel within one small region out of the plurality of small regions and each pixel within a small region adjacent to the one small region. Note that the feature value calculation unit 34a may calculate a value different from the above-described inclination value as the feature value as long as the feature value calculation unit 34a calculates a quantitatively evaluable value for the observation image G1.

The lesion candidate detection unit 34b is configured to include a non-volatile memory (not shown) such as a ROM in which one or more pieces of polyp model information are stored in advance.

Specifically, the polyp model information stored in the memory of the lesion candidate detection unit 34b is configured to include, for example, feature values obtained by quantifying common points and/or similar points in a large number of polyp images.

The lesion candidate detection unit 34b is configured to detect a lesion candidate region L based on a predetermined feature value outputted from the feature value calculation unit 34a and a plurality of pieces of polyp model information read out from the memory, acquire lesion candidate information IL which is information indicating the detected lesion candidate region L, and output the acquired lesion candidate information IL to each of the visibility judgement unit 35 and the display control unit 36.

Specifically, for example, when the feature value of one small region outputted from the feature value calculation unit 34a is coincident with at least one feature value included in the plurality of pieces of polyp model information read out from the memory, the lesion candidate detection unit 34b detects the one small region as the lesion candidate region L. Furthermore, the lesion candidate detection unit 34b acquires the lesion candidate information IL including position information and size information of the lesion candidate region L detected by the above-described method, and outputs the acquired lesion candidate information IL to each of the visibility judgement unit 35 and the display control unit 36.

Note that the position information of the lesion candidate region L is information indicating the position of the lesion candidate region L in the observation image G1, and is acquired, for example, as pixel position of the lesion candidate region L existing in the observation image G1. Furthermore, the size information of the lesion candidate region L is information indicating the size of the lesion candidate region L in the observation image G1, and is acquired, for example, as the number of pixels of the lesion candidate region L existing in the observation image G1.

As long as the region-of-interest detection unit 34 performs the processing for detecting the lesion candidate region L from the observation image G1, the region-of-interest detection unit 34 may not be configured to include the feature value calculation unit 34a and the lesion candidate detection unit 34b. Specifically, the region-of-interest detection unit 34 may be configured to detect the lesion candidate region L from the observation image G1, for example, by performing processing of applying, to the observation image G1, an image discriminator which has beforehand acquired a function capable of identifying a polyp image by a learning method such as deep learning.

Based on the observation image G1 sequentially outputted from the main body device 31, the water feeding instruction detection signal and the air feeding instruction detection signal outputted from the main body device 31, and the lesion candidate information IL outputted from the lesion candidate detection unit 34b, the visibility judgement unit 35 is configured to perform judgement processing as to whether degradation of visibility of the lesion candidate region L corresponding to the lesion candidate information IL is predicted, and output a judgement result obtained by the judgement processing to the display control unit 36. Note that specific processing to be performed in the visibility judgement unit 35 will be described later.

The display control unit 36 is configured to perform processing for generating a display image by using the observation image G1 sequentially outputted from the main body device 31, and perform processing of causing the generated display image to be displayed on the display screen of the display device 41. The display control unit 36 is configured to include an emphasis processing unit 36a for performing emphasis processing to emphasize the lesion candidate region L existing in the observation image G1.

The emphasis processing unit 36a is configured to perform, as emphasis processing, processing for generating a marker image G2 for emphasizing the position of the lesion candidate region L existing in the observation image G1 based on the lesion candidate information IL and adding the marker image G2 to the observation image G1 when a predetermined judgement result (described later) is outputted from the visibility judgement unit 35.

Note that the marker image G2 added by the emphasis processing of the emphasis processing unit 36a may have any form as long as the marker image G2 can present the position of the lesion candidate region L as visual information. In other words, as long as the emphasis processing unit 36a generates the marker image G2 for emphasizing the position of the lesion candidate region L, the emphasis processing unit 36a may perform the emphasis processing by using only the position information included in the lesion candidate information IL. Alternatively, the emphasis processing unit 36a may perform the emphasis processing by using both the position information and the size information included in the lesion candidate information IL.

The display device 41 is configured to include a monitor and the like, and configured to be capable of displaying the display image outputted from the endoscope image processing device 32 on the display screen.

Subsequently, an operation of the present embodiment will be described. For the sake of simplification, the following description will be made by exemplifying a case where one lesion candidate region L1 is included in the observation image G1. The following operation is suitably applied in such a case that the lesion candidate region L1 exists on an inner circumferential surface of a luminal organ, that is, a region of interest exists on an inner circumferential surface of a tubular portion of a subject.

The user connects each part of the endoscope system 1 and turns on the power, and then performs an operation for inserting the insertion portion 22a into a luminal organ of the subject person. In other words, the insertion portion 22a is inserted into the inside of the tubular portion of the subject by a user's manipulation.

With turn-on of a power source of the main body device 31, the endoscope 21 emits illumination light to an object, receives reflected light from the object, picks up an image of the received reflected light to generate an image pickup signal, and outputs the generated image pickup signal to the main body device 31. In other words, the endoscope 21 outputs, to the main body device 31, an image pickup signal obtained by picking up an image of the object inside a tubular portion of the subject.

The main body device 31 (video processor 31b) generates an observation image G1 of the object by performing predetermined processing on the image pickup signal outputted from the endoscope 21, and sequentially outputs the generated observation image G1 frame by frame to the endoscope image processing device 32.

The lesion candidate detection unit 34b detects a lesion candidate region L1 included in the observation image G1 to acquire lesion candidate information IL1 that is information indicating the detected lesion candidate region L1, and outputs the acquired lesion candidate information IL1 to each of the visibility judgement unit 35 and the display control unit 36.

When the lesion candidate information IL1 is not outputted from the lesion candidate detection unit 34b, the display control unit 36 performs processing for causing the observation image G1 outputted from the main body device 31 to be displayed as a display image.

Figure 3:
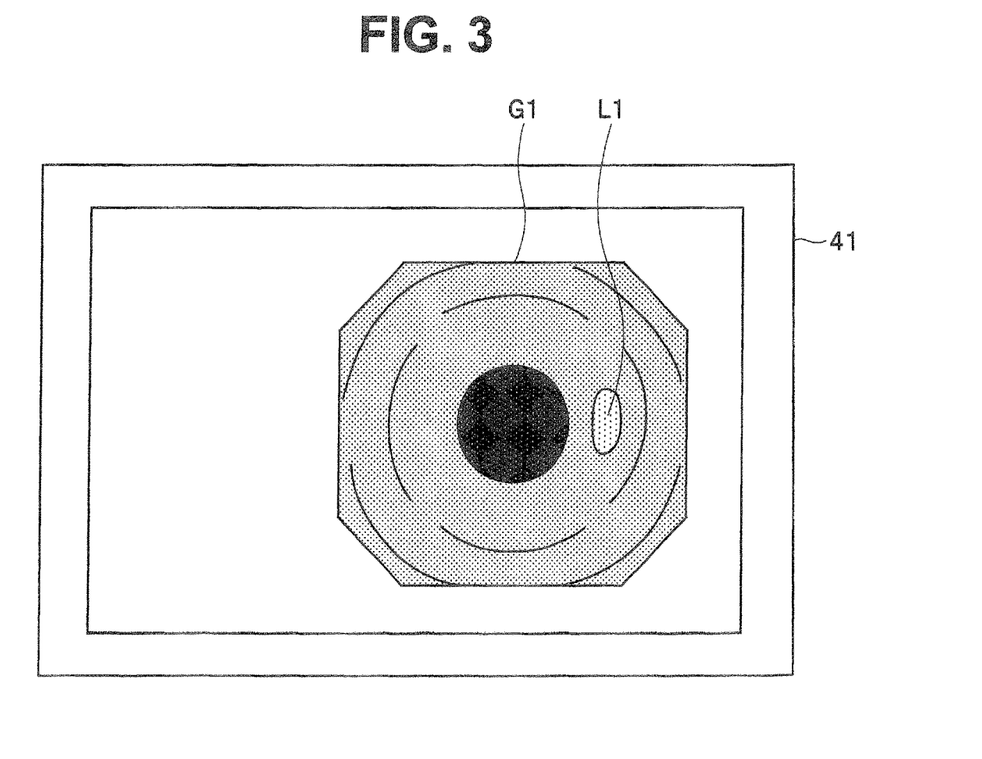
FIG. 3 is a diagram showing an example of a display image which is subjected to processing of the endoscope image processing device according to the embodiment and then displayed on a display device.

When the lesion candidate information IL1 has been outputted from the lesion candidate detection unit 34b and a judgement result indicating that degradation of visibility of the lesion candidate region L1 included in the observation image G1 is not predicted is outputted from the visibility judgement unit 35, for example, as shown in FIG. 3, the display control unit 36 performs processing of causing the observation image G1 outputted from the main body device 31 to be displayed as a display image without causing the emphasis processing unit 36a to perform the emphasis processing. FIG. 3 is a diagram showing an example of the display image which is subjected to the processing of the endoscope image processing device according to the present embodiment and then displayed on the display device.

When the lesion candidate information IL1 has been outputted from the lesion candidate detection unit 34b and a judgement result indicating that degradation of visibility of the lesion candidate region L1 included in the observation image G1 is predicted is outputted from the visibility judgement unit 35, the display control unit 36 performs processing of causing the observation image G1 added with a marker image G2 by the emphasis processing of the emphasis processing unit 36a to be displayed as a display image. In other words, when the judgement result indicating that the degradation of visibility of the lesion candidate region L1 included in the observation image G1 is predicted is outputted from the visibility judgement unit 35, the emphasis processing unit 36a performs emphasis processing of emphasizing the position of the lesion candidate region L1 existing in the observation image G1 based on the lesion candidate information IL.

When the lesion candidate information IL1 is outputted from the lesion candidate detection unit 34b, the visibility judgement unit 35 performs determination processing as to whether degradation of visibility of the lesion candidate region L1 corresponding to the lesion candidate information IL1 is predicted.

Figure 4:
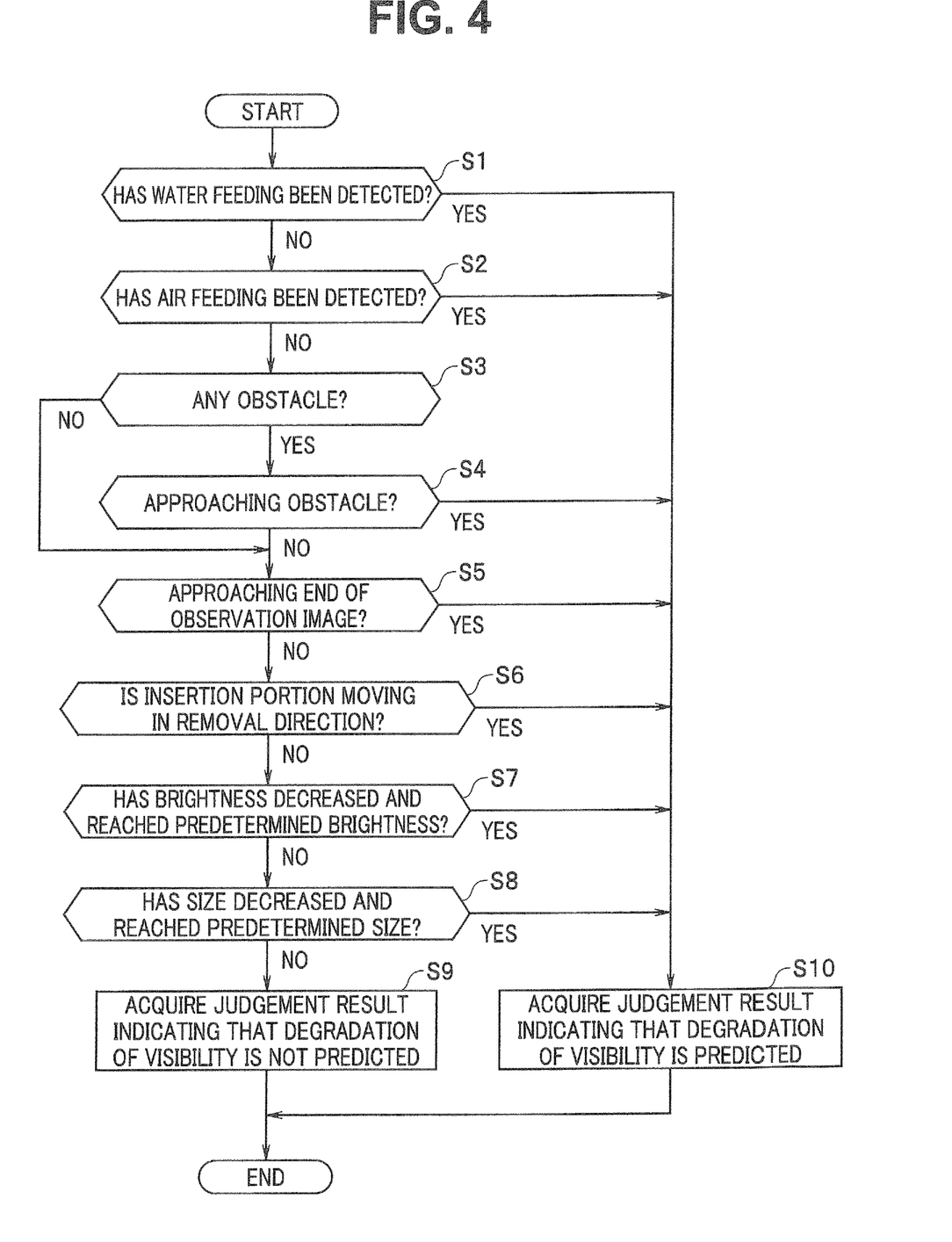
FIG. 4 is a diagram showing an example of the processing performed in the endoscope image processing device according to the embodiment.

Here, a specific example of the judgement processing performed by the visibility judgement unit 35 of the present embodiment will be described with reference to FIG. 4 and the like. FIG. 4 is a diagram showing an example of processing performed in the endoscope image processing device according to the embodiment.

The visibility judgement unit 35 performs processing of detecting the presence or absence of water feeding to the lesion candidate region L1 included in the observation image G1 based on the observation image G1 sequentially outputted from the main body device 31, the water feeding instruction detection signal outputted from the main body device 31, and the lesion candidate information IL1 outputted from the lesion candidate detection unit 34b (step S1 in FIG. 4).

When the visibility judgement unit 35 detects water feeding to the lesion candidate region L1 included in the observation image G1 (S1: YES), the visibility judgement unit 35 acquires a judgement result indicating that the degradation of visibility of the lesion candidate region L1 is predicted, and outputs the judgement result to the display control unit 36 (step S10 of FIG. 4). When the visibility judgement unit 35 cannot detect water feeding to the lesion candidate region L1 included in the observation image G1 (S1: NO), the visibility judgement unit 35 proceeds to perform processing of step S2 in FIG. 4 described later.

Specifically, for example, when the water feeding instruction detection signal is outputted from the main body device 31, based on a processing result obtained by performing predetermined image processing on the observation image G1 and the lesion candidate information IL1 outputted from the lesion candidate detection unit 34b, the visibility judgement unit 35 detects whether water jetted from the distal end portion of the insertion portion 22a is applied to the lesion candidate region L1 or a neighborhood of the lesion candidate region L1. Then, when the visibility judgement unit 35 detects that the water jetted from the distal end portion of the insertion portion 22a is applied to the lesion candidate region L1 included in the observation image G1 or the neighborhood of the lesion candidate region L1, the visibility judgement unit 35 acquires the judgement result indicating that the degradation of visibility of the lesion candidate region L1 is predicted. Furthermore, when the visibility judgement unit 35 detects that the water jetted from the distal end portion of the insertion portion 22a is applied to neither the lesion candidate region L1 included in the observation image G1 nor the neighborhood of the lesion candidate region L1, the visibility judgement unit 35 proceeds to perform the processing of step S2 of FIG. 4 described later.

Note that the visibility judgement unit 35 may acquire a judgment result indicating that degradation of visibility of the lesion candidate region L1 included in the observation image G1 is predicted, for example, when the output of the water feeding instruction detection signal from the main body device 31 is detected.

Figure 5A:
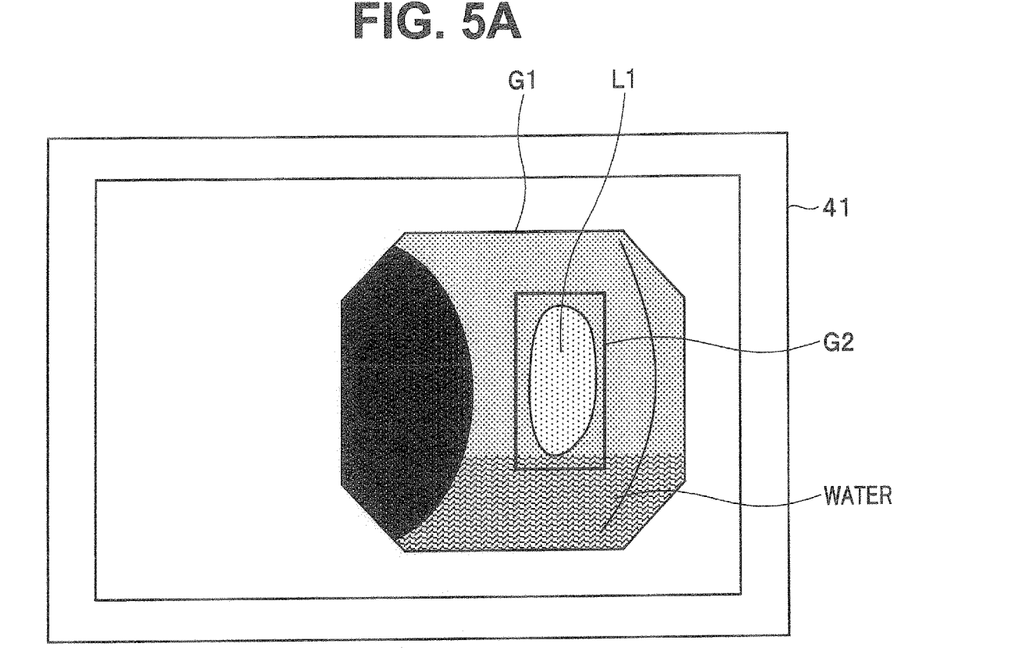
FIG. 5A is a diagram showing an example of the display image which is subjected to the processing of the endoscope image processing device according to the embodiment and then displayed on the display device.
Figure 5B:
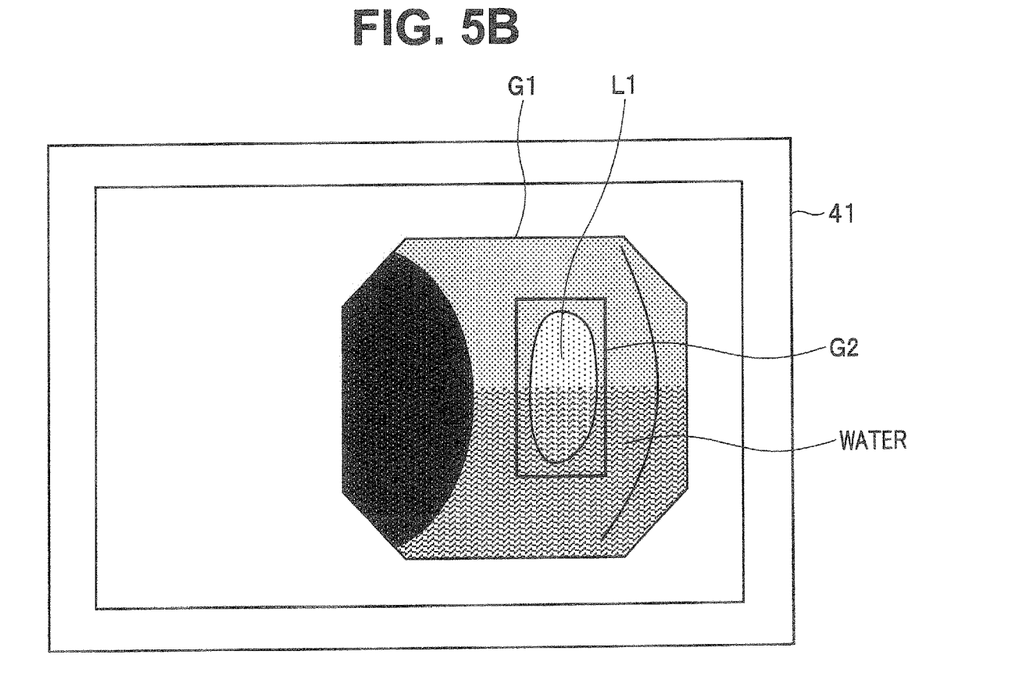
FIG. 5B is a diagram showing an example of the display image which is subjected to the processing of the endoscope image processing device according to the embodiment and then displayed on the display device.

When the judgment result indicating that the degradation of visibility of the lesion candidate region L1 is predicted is obtained by the processing of step S1 in FIG. 4, the emphasis processing for adding the observation image G1 with the marker image G2 is started, for example, at a timing either when water jetted from the distal end portion of the insertion portion 22a is applied to the neighborhood of the lesion candidate region L1 included in the observation image G1 (see FIG. 5A) or just after the water feeding switch of the operation unit 22b is pushed. Furthermore, when the judgement result indicating that the degradation of visibility of the lesion candidate region L1 is predicted is obtained by the processing of step S1 of FIG. 4, the emphasis processing for adding the observation image G1 with the marker image G2 is continued, for example, either during a time period when water jetted from the distal end portion of the insertion portion 22a is applied to at least a part of the lesion candidate region L1 included in the observation image G1 (FIG. 5B) or a time period when the water feeding switch of the operation unit 22b is pushed. FIG. 5A and FIG. 5B are diagrams showing an example of a display image which is subjected to the processing of the endoscope image processing device according to the present embodiment and then displayed on the display device.

The visibility judgement unit 35 performs processing for detecting the presence or absence of air feeding to the lesion candidate region L1 included in the observation image G1 based on the air feeding instruction detection signal outputted from the main body device 31 (step S2 of FIG. 4).

When the visibility judgement unit 35 detects air feeding to the lesion candidate region L1 included in the observation image G1 (S2: YES), the visibility judgement unit 35 acquires a judgement result indicating that degradation of visibility of the lesion candidate region L1 is predicted, and outputs the judgement result to the display control unit 36 (step S10 in FIG. 4). When the visibility judgement unit 35 cannot detect air feeding to the lesion candidate region L1 included in the observation image G1 (S2: NO), the visibility judgement unit 35 proceeds to perform the processing of step S3 in FIG. 4 described later.

When the judgement result indicating that the degradation of visibility of the lesion candidate region L1 is predicted is obtained by the processing of step S2 in FIG. 4, the emphasis processing for adding the observation image G1 with the marker image G2 is started, for example, at a timing just after the air feeding switch of the operation unit 22b is pushed. Furthermore, when the judgement result indicating that the degradation of visibility of the lesion candidate region L1 is predicted is obtained by the processing of step S2 of FIG. 4, the emphasis processing for adding the observation image G1 with the marker image G2 is continued, for example, during a time period when the air feeding switch of the operation unit 22b continues to be pushed.

Based on the processing result obtained by performing the predetermined image processing on the observation image G1 sequentially outputted from the main body device 31 and the lesion candidate information IL1 outputted from the lesion candidate detection unit 34b, the visibility judgement unit 35 performs processing of detecting the presence or absence of an obstacle which is an object covering the entire lesion candidate region L1 in the observation image G1, such as a fold, a residue, blood, a treatment instrument or the like in a large intestine (step S3 of FIG. 4).

When the visibility judgement unit 35 detects the presence of an obstacle in the observation image G1 (S3: YES), the visibility judgement unit 35 proceeds to perform the processing of step S4 in FIG. 4 described later. When the visibility judgement unit 35 cannot detect the presence of an obstacle in the observation image G1 (S3: NO), the visibility judgement unit 35 proceeds to perform the processing of step S5 in FIG. 4 described later.

Based on a motion vector (change in position) of the obstacle detected by the processing of step S3 in FIG. 4 and a motion vector (change in position) of the center of gravity of the lesion candidate region L1 obtained based on the position information included in the lesion candidate information IL1 outputted from the lesion candidate detection unit 34b, the visibility judgement unit 35 performs processing for detecting whether the lesion candidate region L1 is approaching the obstacle (step S4 of FIG. 4).

When the visibility judgement unit 35 detects that the lesion candidate region L1 is approaching the obstacle detected by the processing of step S3 in FIG. 4 (S4: YES), the visibility judgement unit 35 acquires a judgement result indicating that degradation of visibility of the lesion candidate region L1 is predicted, and outputs the judgement result to the display control unit 36 (step S10 in FIG. 4). Furthermore, when the visibility judgement unit 35 detects either that the lesion candidate region L1 is being away from the obstacle detected by the processing of step S3 in FIG. 4 or that the position of the lesion candidate region L1 has not changed (S4: NO), the visibility judgement unit 35 proceeds to perform processing of step S5 in FIG. 4 described later. In other words, when the visibility judgement unit 35 detects such a positional change of the lesion candidate region L1 that the lesion candidate region L1 is approaching the obstacle which covers the entire lesion candidate region L1 in the observation image G1, the visibility judgement unit 35 acquires a judgement result indicating that degradation of visibility of the lesion candidate region L1 included in the observation image G1 is predicted.

Figure 6A:
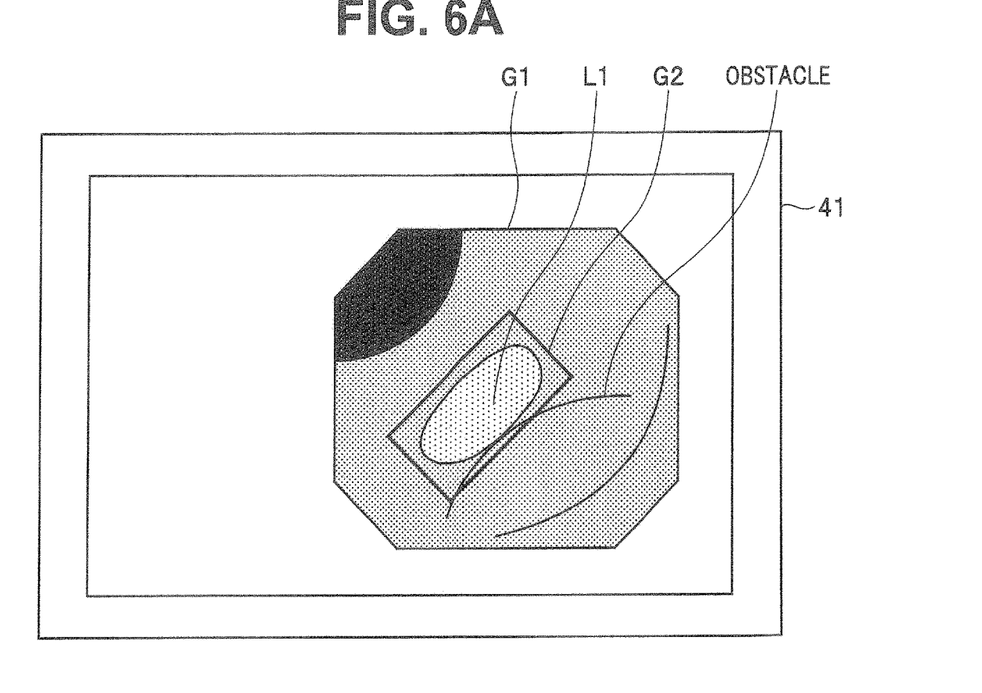
FIG. 6A is a diagram showing an example of the display image which is subjected to the processing of the endoscope image processing device according to the embodiment and then displayed on the display device.
Figure 6B:
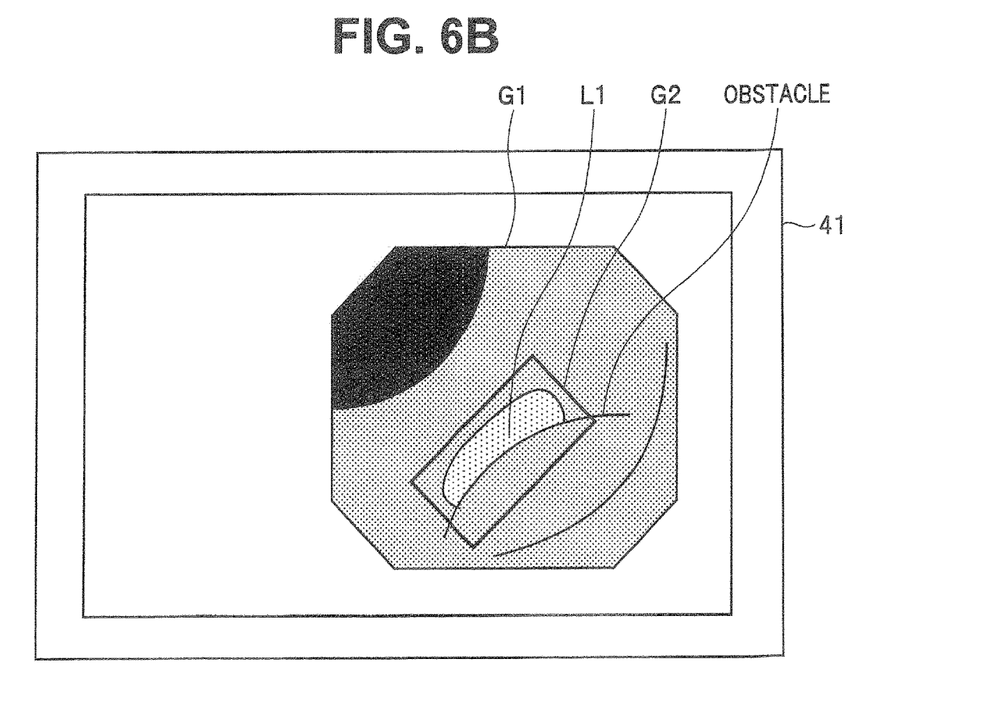
FIG. 6B is a diagram showing an example of the display image which is subjected to the processing of the endoscope image processing device according to the embodiment and then displayed on the display device.

When the judgement result indicating that the degradation of visibility of the lesion candidate region L1 is predicted is acquired by the processing of step S4 in FIG. 4, the emphasis processing of adding the observation image G1 with the marker image G2 is started, for example, at a timing when the lesion candidate region L1 included in the observation image G1 moves to a position adjacent to the obstacle in the observation image G1 (see FIG. 6A). When the judgement result indicating that the degradation of visibility of the lesion candidate region L1 is predicted is acquired by the processing of step S4 in FIG. 4, the emphasis processing for adding the observation image G1 with the marker image G2 is continued, for example, during a time period when at least a part of the lesion candidate region L1 is covered by the obstacle in the observation image G1 (see FIG. 6B). FIGS. 6A and 6B are diagrams showing an example of a display image which is subjected to the processing of the endoscope image processing device according to the embodiment and then displayed on the display device.

Note that in the present embodiment, when the emphasis processing for adding the marker image G2 is started after the processing of step S4 of FIG. 4, the emphasis processing may be stopped, for example, at a timing when the entire lesion candidate region L1 included in the observation image G1 is covered by the obstacle in the observation image G1, or the emphasis processing may be stopped after a predetermined time has elapsed since the entire lesion candidate region L1 is covered by the obstacle.

Based on the observation image G1 sequentially outputted from the main body device 31 and the motion vector (change in position) of the center of gravity of the lesion candidate region L1 obtained based on the position information included in the lesion candidate information IL1 outputted from the lesion candidate detection unit 34b, the visibility judgement unit 35 performs processing of detecting whether the lesion candidate region L1 is approaching an end of the observation image G1 (step S5 in FIG. 4).

When the visibility judgement unit 35 detects that the lesion candidate region L1 is approaching the end of the observation image G1 (S5: YES), the visibility judgement unit 35 acquires a judgement result indicating that degradation of visibility of the lesion candidate region L1 is predicted, and outputs the judgement result to the display control unit 36 (step S10 in FIG. 4). When the visibility judgement unit 35 detects either that the lesion candidate region L1 is being away from the end of the observation image G1 or that the position of the lesion candidate region L1 has not changed (S5: NO), the visibility judgement unit 35 proceeds to perform processing of step S6 of FIG. 4 described later. In other words, when the visibility judgement unit 35 detects such a positional change of the lesion candidate region L1 that the lesion candidate region L1 is approaching the end of the observation image G1, the visibility judgement unit 35 acquires a judgement result indicating that the degradation of visibility of the lesion candidate region L1 included in the observation image G1 is predicted.

Figure 7A:
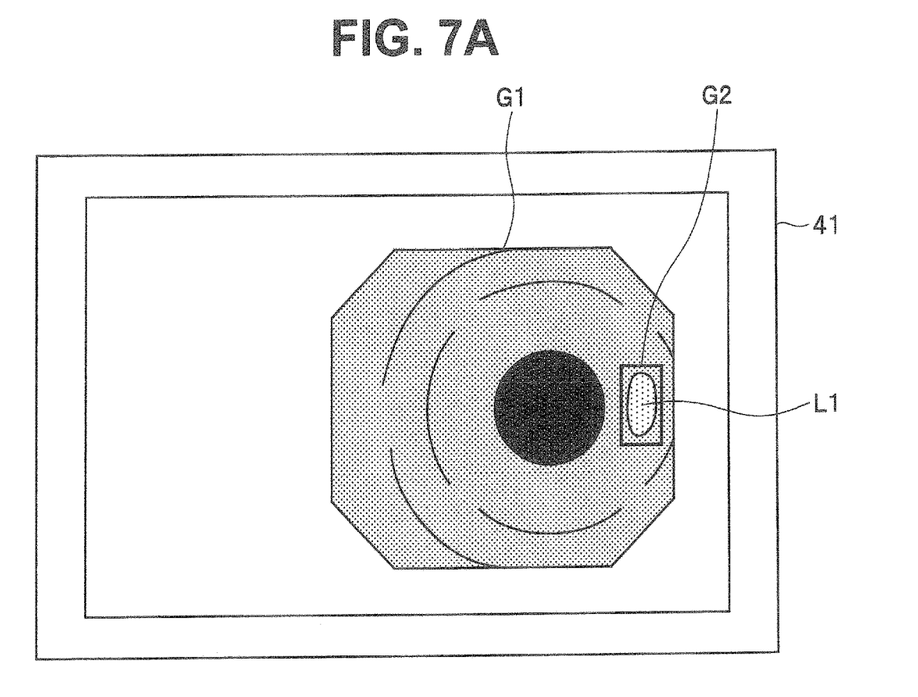
FIG. 7A is a diagram showing an example of the display image which is subjected to the processing of the endoscope image processing device according to the embodiment and then displayed on the display device.
Figure 7B:
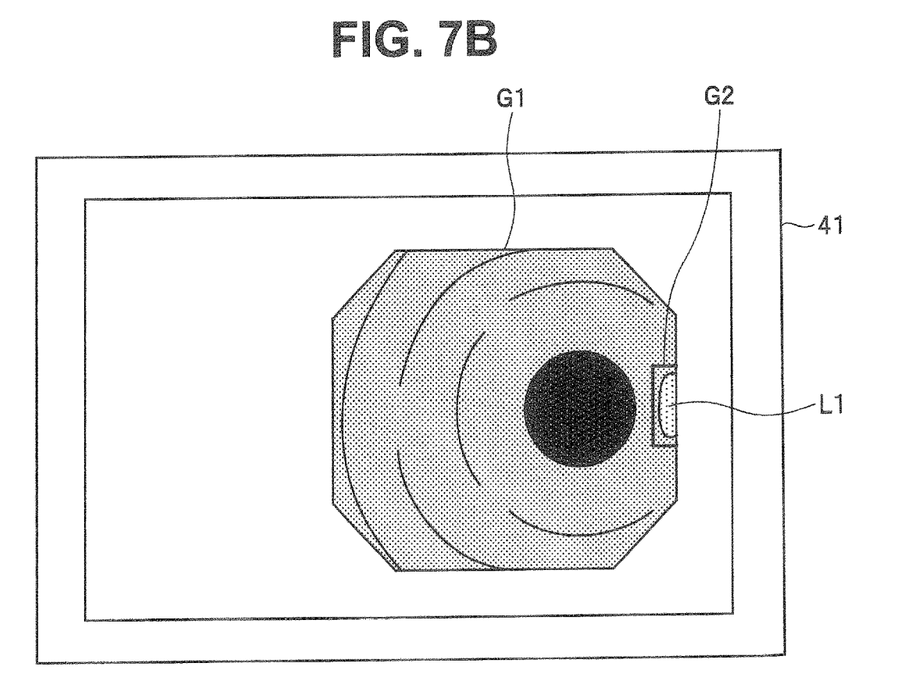
FIG. 7B is a diagram showing an example of the display image which is subjected to the processing of the endoscope image processing device according to the embodiment and then displayed on the display device.

When the judgement result indicating that the degradation of visibility of the lesion candidate region L1 is predicted is acquired by the processing of step S5 of FIG. 4, the emphasis processing for adding the observation image G1 with the marker image G2 is started, for example, at a timing when the lesion candidate region L1 included in the observation image G1 enters a predetermined region corresponding to an end portion of the observation image G1 (see FIG. 7A). Furthermore, when the judgement result indicating that the degradation of visibility of the lesion candidate region L1 is predicted is acquired by the processing of step S5 in FIG. 4, the emphasis processing for adding the observation image G1 with the marker image G2 is continued, for example, during a time period when at least a part of the lesion candidate region L1 exists in the predetermined region corresponding to the end portion of the observation image G1 (see FIG. 7B). FIGS. 7A and 7B are diagrams showing an example of a display image which is subjected to the processing of the endoscope image processing device according to the embodiment, and then displayed on the display device.

The visibility judgement unit 35 performs processing for detecting whether the insertion portion 22a is moving in a direction in which the insertion portion 22a is removed from the inside of a luminal organ based on the observation image G1 sequentially outputted from the main body device 31 (step S6 in FIG. 4).

Specifically, the visibility judgement unit 35 performs processing using an optical flow of the observation image G1 which is a vector field configured by motion vectors of all pixels included in the observation image G1 sequentially outputted from the main body device 31, thereby detecting whether the insertion portion 22a is moving in a direction in which the insertion portion 22a is removed from the inside of the luminal organ.

When the visibility judgement unit 35 detects that the insertion portion 22a is moving in the direction in which the insertion portion 22a is removed from the inside of the luminal organ (S6: YES), the visibility judgement unit 35 acquires the judgement result indicating that degradation of visibility of the lesion candidate region L1 is predicted, and outputs the judgement result to the display control unit 36 (step S10 in FIG. 4). When the visibility judgement unit 35 detects either that the insertion portion 22a is moving in a direction in which the insertion portion 22a is inserted into a deep part of the luminal organ or that the insertion portion 22a is stopped (S6: NO), the visibility judgement unit 35 proceeds to perform processing of step S7 in FIG. 4 described later.

When the judgement result indicating that the degradation of visibility of the lesion candidate region L1 is predicted is acquired by the processing of step S6 in FIG. 4, the emphasis processing for adding the observation image G with the marker image G2 is started, for example, at a timing when the lesion candidate region L1 included in the observation image G1 starts to move from a front side to a back side in the observation image G1. Furthermore, when the judgement result indicating that the degradation of visibility of the lesion candidate region L1 is predicted is acquired by the processing of step S6 of FIG. 4, the emphasis processing for adding the observation image G1 with the marker image G2 is continued, for example, during a time period when the lesion candidate region L1 continues to move from the front side to the back side in the observation image G1.

Note that according to the present embodiment, the processing as described above is not limited to the processing performed in step S6 of FIG. 4, and, for example, such processing as detects, based on the optical flow of the observation image G1 and the lesion candidate information IL1 outputted from the lesion candidate detection unit 34b, whether the lesion candidate region L1 included in the observation image G1 is moving from the front side to the back side in the observation image G1 may be performed in step S6 in FIG. 4. It may be set for such processing that when it is detected that the lesion candidate region L1 is moving from the front side to the back side in the observation image G1, a judgement result indicating that degradation of visibility of the lesion candidate region L1 is predicted is acquired.

Based on the observation image G1 sequentially outputted from the main body device 31 and the lesion candidate information IL1 outputted from the lesion candidate detection unit 34b, the visibility judgement unit 35 performs processing for detecting whether the brightness of the lesion candidate region L1 included in the observation image G1 has decreased and reached a predetermined brightness (step S7 in FIG. 4).

When the visibility judgement unit 35 detects that the brightness of the lesion candidate region L1 has decreased and reached the predetermined brightness (S7: YES), the visibility judgement unit 35 acquires a judgement result indicating that the degradation of visibility of the lesion candidate region L1 is predicted, and outputs the judgement result to the display control unit 36 (step S10 in FIG. 4). When the visibility judgement unit 35 detects either that the brightness of the lesion candidate region L1 has increased or that the brightness of the lesion candidate region L1 has not decreased until it has reached the predetermined brightness (step S5: NO), the visibility judgement unit 35 proceeds to perform processing of step S8 in FIG. 4 described later.

Specifically, the visibility judgement unit 35 performs, for example, processing of specifying the lesion candidate region L1 in the observation image G1 based on the position information included in the lesion candidate information ILL and also detecting whether an average brightness value AVB of respective pixels of the specified lesion candidate region L1 has decreased and reached a predetermined brightness value TB. When the visibility judgement unit 35 detects that the average brightness value AVB of the respective pixels of the lesion candidate region L1 has decreased and reached the predetermined brightness value TB, the visibility judgement unit 35 acquires a judgement result indicating that the degradation of visibility of the lesion candidate region L1 is predicted. Furthermore, when the visibility judgement unit 35 detects that the average brightness value AVB has increased or the average brightness value AVB has not decreased until the average brightness value AVB has reached the predetermined brightness value TB, the visibility judgement unit 35 proceeds to perform the processing of step S8 of FIG. 4 described later. Note that the predetermined brightness value TB may be appropriately set, for example, as a brightness value corresponding to a lower limit of brightness which makes it possible to secure the visibility of the lesion candidate region L1 included in the observation image G1.

Note that according to the present embodiment, for example, processing for detecting whether the brightness of a neighborhood of the lesion candidate region L1 in the observation image G1 has decreased and reached a predetermined brightness may be performed in step S7 of FIG. 4. Furthermore, when it is detected according to the processing as described above that the brightness of the neighborhood of the lesion candidate region L1 in the observation image G1 has decreased and reached the predetermined brightness, a judgement result indicating that the degradation of visibility of the lesion candidate region L1 is predicted may be acquired. According to the present embodiment, for example, processing for detecting whether a contrast value of the lesion candidate region L1 included in the observation image G1 has decreased and reached a predetermined contrast value may be performed in step S7 of FIG. 4. Furthermore, when it is detected according to the processing as described above that the contrast value of the lesion candidate region L1 included in the observation image G1 has decreased and reached the predetermined contrast value, a judgement result indicating that the degradation of visibility of the lesion candidate region L1 is predicted may be acquired. According to the present embodiment, for example, processing for detecting whether the contrast value of a neighborhood of the lesion candidate region L1 in the observation image G1 has decreased and reached a predetermined contrast value may be performed in step S7 of FIG. 4. When it is detected according to the processing as described above that the contrast value of the neighborhood of the lesion candidate region L1 in the observation image G1 has decreased and reached the predetermined contrast value, a judgement result indicating that the degradation of visibility of the lesion candidate region L1 is predicted may be acquired.

The visibility judgement unit 35 performs processing for detecting whether the size has reached a predetermined size with decreasing of the size of the lesion candidate region L1 included in the observation image G1 (the shape changes) based on the size information included in the lesion candidate information IL1 outputted from the lesion candidate detection unit 34b (step S8 in FIG. 4).

When the visibility judgement unit 35 detects that the size of the lesion candidate region L1 has decreased and reached a predetermined size (S8: YES), the visibility judgement unit 35 acquires a judgement result indicating that degradation of visibility of the lesion candidate region L1 is predicted, and outputs the judgement result to the display control unit 36 (step S10 in FIG. 4). When the visibility judgement unit 35 detects that the size of the lesion candidate region L1 has increased or the size of the lesion candidate region L1 has not decreased until the size of the lesion candidate region L1 has reached the predetermined size (S8: NO), the visibility judgement unit 35 acquires a judgement result indicating that the degradation of visibility of the lesion candidate region L1 is not predicted, and outputs the judgement result to the display control unit 36 (step S9 in FIG. 4).

Note that according to the present embodiment, for example, processing for detecting whether the shape of the lesion candidate region L1 included in the observation image G1 has changed to a predetermined shape may be performed in step S8 of FIG. 4. Furthermore, when it is detected according to the processing as described above that the shape of the lesion candidate region L1 included in the observation image G1 has changed to a predetermined shape, a judgment result indicating that the degradation of visibility of the lesion candidate region L1 is predicted may be acquired.

In the present embodiment, as long as it is possible to acquire a judgement result as to whether degradation of visibility of the lesion candidate region L1 is predicted, for example, some of the respective processing exemplified in FIG. 4 may be omitted as appropriate, the order of the respective processing exemplified in FIG. 4 may be rearranged as appropriate, or two or more of the respective processing exemplified in FIG. 4 may be performed in parallel.

In other words, based on at least one of the change of the lesion candidate region L1 included in the observation image G1 and the change in a region in the neighborhood of the lesion candidate region L1, the visibility judgement unit 35 of the present embodiment performs judgement processing as to whether degradation of visibility of the lesion candidate region L1 is predicted. Specifically, the visibility judgement unit 35 of the present embodiment performs the judgement processing as to whether the degradation of visibility of the lesion candidate region L1 is predicted, based on a detection result obtained by detecting at least any of the change in position of the lesion candidate region L1 included in the observation image G1, the change in brightness of the lesion candidate region L1, the change in shape of the lesion candidate region L1, the change in contrast of the lesion candidate region L1, and the change in size of the lesion candidate region L1.

Based on at least one of a function state and an operation state of the endoscope 21 configured to pick up an image of an object including a lesion candidate region L1, the visibility judgement unit 35 of the present embodiment performs judgement processing as to whether degradation of visibility of the lesion candidate region L1 is predicted. Specifically, the visibility judgement unit 35 of the present embodiment performs the judgement processing as to whether degradation of visibility of a lesion candidate region L1 is predicted, based on a detection result obtained by detecting at least any one of the presence or absence of water feeding from the endoscope 21 to the lesion candidate region L1, the presence or absence of air feeding from the endoscope 21 to the lesion candidate region L1, and a moving direction of the insertion portion 22a to be inserted into a luminal organ in the endoscope 21.

As described above, according to the present embodiment, when degradation of visibility of a lesion candidate region L included in an observation image G1 is predicted, it is possible to display a display image in which a marker image G2 for emphasizing the position of the lesion candidate region L is added to the observation image G1. Therefore, according to the present embodiment, even in a situation where visibility of a region of interest such as a lesioned part or the like existing in an observation image may degrade, it is possible to prevent oversight of the region of interest. Furthermore, according to the present embodiment, for example, when a lesion candidate region L exists on an inner peripheral surface of a luminal organ, that is, when the lesion candidate region L included in an observation image G1 and a region around the lesion candidate region in the observation image G1 move simultaneously together while following the insertion and removal of the insertion portion 22a, it is possible to prevent the lesion candidate region L from being overlooked.

As described above, according to the present embodiment, when degradation of visibility of a lesion candidate region L included in an observation image G1 is not predicted, a marker image G2 for emphasizing the position of the lesion candidate region L is not added to the observation image G1. Therefore, according to the present embodiment, for example, when a user performs a work for visually searching for the presence or absence of a lesioned part in an observation image, it is possible not to hinder achievement of the skill meeting the work, and also not to lower user's motivation for the work.

Note that the present invention is not limited to the above-described embodiment, and it goes without saying that various modifications and applications can be made without departing from the subject matter of the invention.

The endoscope image processing device and the like according to the present embodiment may include a processor and a storage (e.g., a memory). The functions of individual units in the processor may be implemented by respective pieces of hardware or may be implemented by an integrated piece of hardware, for example. The processor may include hardware, and the hardware may include at least one of a circuit for processing digital signals and a circuit for processing analog signals, for example. The processor may include one or a plurality of circuit devices (e.g., an IC) or one or a plurality of circuit elements (e.g., a resistor, a capacitor) on a circuit board, for example. The processor may be a CPU (central processing unit), for example, but this should not be construed in a limiting sense, and various types of processors including a GPU (graphics processing unit) and a DSP (digital signal processor) may be used. The processor may be a hardware circuit with an ASIC (application specific integrated circuit) or an FPGA (field-programmable gate array). The processor may include an amplification circuit, a filter circuit, or the like for processing analog signals. The memory may be a semiconductor memory such as an SRAM and a DRAM; a register; a magnetic storage device such as a hard disk device; and an optical storage device such as an optical disk device. The memory stores computer-readable instructions, for example. When the instructions are executed by the processor, the functions of each unit of the image processing device and the like are implemented. The instructions may be a set of instructions constituting a program or an instruction for causing an operation on the hardware circuit of the processor.

The units in the endoscope image processing device and the like and the display apparatus according to the present embodiment may be connected with each other via any types of digital data communication such as a communication network or via communication media. The communication network may include a LAN (local area network), a WAN (wide area network), and computers and networks which form the internet, for example.

What is claimed is:

1. An endoscope image processing device comprising a processor, the processor sequentially receiving an observation image obtained by performing image pickup of an object inside a tubular portion of a subject, and the processor being configured to perform processing comprising:
    detecting processing for detecting a region of interest included in the observation image;
    judgement processing for judging whether degradation of visibility of the region of interest included in the observation image is predicted; and
    emphasis processing for emphasizing a position of the region of interest in response to a judgement result in the judgement processing indicating that the degradation of visibility of the region of interest included in the observation image is predicted.

2. The endoscope image processing device according to claim 1, wherein the processor performs the judgement processing based on at least one of a change of the region of interest included in the observation image and a change of a region near the region of interest.

3. The endoscope image processing device according to claim 2, wherein the processor performs the judgement processing based on a detection result obtained by detecting a change in position of the region of interest.

4. The endoscope image processing device according to claim 3, wherein the processor is configured to:
    detect an obstacle that can cover an entirety of the region of interest in the observation image,
    determine whether the detected obstacle and the region of interest are approaching each other, and
    in response to determining that the detected obstacle and the region of interest are approaching each other, acquire the judgment result indicating that degradation of visibility of the region of interest included in the observation image is predicted.

5. The endoscope image processing device according to claim 3, wherein the processor is configured to:
    determine whether the position of the region of interest approaches an end of the observation image, and
    in response to determining that the position of the region of interest approaches the end of the observation image, acquire the judgement result indicating that degradation of visibility of the region of interest included in the observation image is predicted.

6. The endoscope image processing device according to claim 2, wherein:
    the processor performs the judgement processing based on a detection result obtained by detecting a change in at least one of a brightness of the region of interest and a brightness of a neighborhood of the region of interest, and
    the processor acquires the judgement result indicating that the degradation of visibility of the region of interest included in the observation image is predicted when the detection result indicates that the at least one of the brightness of the region of interest and the brightness of the neighborhood of the region of interest has decreased and reached a predetermined brightness.

7. The endoscope image processing device according to claim 2, wherein:
    the processor performs the judgement processing based on a detection result obtained by detecting a change in at least one of a contrast of the region of interest and a contrast of a neighborhood of the region of interest, and
    the processor acquires the judgement result indicating that the degradation of visibility of the region of interest included in the observation image is predicted when the detection result indicates that the at least one of the contrast of the region of interest and the contrast of the neighborhood of the region of interest has decreased and reached a predetermined contrast value.

8. The endoscope image processing device according to claim 2, wherein:
    the processor performs the judgement processing based on a detection result obtained by detecting a change in a shape of the region of interest, and
    the processor acquires the judgement result indicating that the degradation of visibility of the region of interest included in the observation image is predicted when the detection result indicates that the shape of the region of interest has changed to a predetermined shape.

9. The endoscope image processing device according to claim 2, wherein:
    the processor performs the judgement processing based on a detection result obtained by detecting a change in a size of the region of interest, and
    the processor acquires the judgement result indicating that the degradation of visibility of the region of interest included in the observation image is predicted when the detection result indicates that the size of the region of interest has decreased and reached a predetermined size.

10. The endoscope image processing device according to claim 1, wherein the processor performs the judgement processing based on at least one of a function state and an operation state of an endoscope configured to pick up an image of the object including the region of interest.

11. The endoscope image processing device according to claim 10, wherein the processor performs the judgement processing based on a detection result obtained by detecting a moving direction of an insertion portion to be inserted into the tubular portion in the endoscope.

12. The endoscope image processing device according to claim 11, wherein when the processor detects that the insertion portion moves in a direction in which the insertion portion is removed from an inside of the tubular portion, the processor acquires the judgement result indicating that degradation of visibility of the region of interest included in the observation image is predicted.

13. The endoscope image processing device according to claim 10, wherein the processor performs the judgement processing based on a detection result obtained by detecting presence or absence of water feeding from the endoscope to the region of interest.

14. The endoscope image processing device according to claim 13, wherein the processor detects the presence or absence of water feeding from the endoscope to the region of interest based on a processing result obtained by performing image processing on the observation image.

15. The endoscope image processing device according to claim 10, wherein the processor performs the judgement processing based on a detection result obtained by detecting presence or absence of air feeding from the endoscope to the region of interest.

16. The endoscope image processing device according to claim 1, wherein the region of interest exists on an inner peripheral surface of the tubular portion.

17. The endoscope image processing device according to claim 1, wherein the processor performs the emphasis processing by presenting the position of the region of interest as visual information.

18. The endoscope image processing device according to claim 17, wherein the processor performs the emphasis processing by adding the visual information to the observation image at a position associated with the position of the region of interest.

19. The endoscope image processing device according to claim 18, wherein the processor performs the emphasis processing by adding, as the visual information, a marker to the observation image.

20. An endoscope image processing method comprising:

performing processing for detecting a region of interest included in an observation image obtained by performing image pickup of an object inside a tubular portion of an object;

performing judgment processing for judging whether degradation of visibility of the region of interest included in the observation image is predicted; and performing emphasis processing for emphasizing a position of the region of interest in response to a judgement result in the judgement processing indicating that the degradation of visibility of the region of interest included in the observation image is predicted.

\* \* \* \* \*